United States Patent
Girgis et al.

(10) Patent No.: US 10,486,131 B2
(45) Date of Patent: Nov. 26, 2019

(54) INTEGRATED REACTOR SYSTEM FOR IONIC LIQUID-CATALYZED HYDROCARBON CONVERSION

(71) Applicant: Chevron U.S.A. Inc., San Ramon, CA (US)

(72) Inventors: Michael John Girgis, Richmond, CA (US); Huping Luo, Richmond, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 272 days.

(21) Appl. No.: 15/794,104

(22) Filed: Oct. 26, 2017

(65) Prior Publication Data

US 2019/0126232 A1    May 2, 2019

(51) Int. Cl.
| | |
|---|---|
| *B01J 19/24* | (2006.01) |
| *B01J 19/26* | (2006.01) |
| *C07C 2/58* | (2006.01) |
| *B01J 4/00* | (2006.01) |
| *B01J 19/00* | (2006.01) |

(52) U.S. Cl.
CPC .......... *B01J 19/2405* (2013.01); *B01J 4/002* (2013.01); *B01J 19/006* (2013.01); *B01J 19/24* (2013.01); *B01J 19/26* (2013.01); *C07C 2/58* (2013.01); *B01J 2219/00081* (2013.01); *B01J 2219/00763* (2013.01); *B01J 2219/182* (2013.01); *B01J 2219/185* (2013.01); *B01J 2219/24* (2013.01)

(58) Field of Classification Search
None
See application file for complete search history.

(56) References Cited

U.S. PATENT DOCUMENTS

| | | | | | |
|---|---|---|---|---|---|
| 2,937,079 | A | * | 5/1960 | Van Pool | B01D 11/043 422/201 |
| 3,006,739 | A | * | 10/1961 | Van Pool | B01D 11/043 422/201 |
| 3,133,128 | A | * | 5/1964 | McDonald | B01J 19/26 585/720 |
| 3,435,092 | A | * | 3/1969 | Hutson, Jr. | C07C 2/62 585/720 |

(Continued)

FOREIGN PATENT DOCUMENTS

| | | |
|---|---|---|
| DE | 2301636 A1 | 9/1973 |
| GB | 577581 A | 5/1946 |

OTHER PUBLICATIONS

M. Zhang, et al., Mixing and separation of liquid-liquid two-phase in a novel cyclone reactor of isobutane alkylation catalyzed by ionic liquid, Powder Technol. (2017), http://dx.doi.org/10.1016/j.powtec.2017.01.009.

(Continued)

*Primary Examiner* — Jennifer A Leung
(74) *Attorney, Agent, or Firm* — Susan M. Abernathy; Terrence Flaherty (57) ABSTRACT

An integrated reactor system for performing an ionic liquid-catalyzed hydrocarbon conversion is provided. The integrated reactor system provides intimate and rapid mixing between hydrocarbon reactants and ionic liquid catalysts while simultaneously removing reaction heat with a heat exchanger that is internal to the hydrocarbon conversion reactor.

22 Claims, 6 Drawing Sheets
(6 of 6 Drawing Sheet(s) Filed in Color)

(56) References Cited

U.S. PATENT DOCUMENTS

| | | | |
|---|---|---|---|
| 3,501,536 A | | 3/1970 | Borst, Jr. |
| 4,156,457 A | * | 5/1979 | Murray .................. B01D 53/14 165/143 |
| 5,120,895 A | | 6/1992 | Child et al. |
| 6,028,024 A | | 2/2000 | Hirschauer et al. |
| 6,106,789 A | | 8/2000 | Thompson et al. |
| 7,285,698 B2 | | 10/2007 | Liu et al. |
| 7,432,408 B2 | | 10/2008 | Timken et al. |
| 7,432,409 B2 | | 10/2008 | Elomari et al. |
| 7,919,663 B2 | | 4/2011 | Hommeltoft et al. |
| 7,919,664 B2 | | 4/2011 | Hommeltoft et al. |
| 8,252,968 B2 | | 8/2012 | Hommeltoft et al. |
| 9,388,093 B2 | | 7/2016 | Luo et al. |
| 2003/0060359 A1 | | 3/2003 | Olivier-Bourbigou et al. |
| 2003/0192683 A1 | | 10/2003 | Menon et al. |
| 2004/0077914 A1 | | 4/2004 | Zavilla et al. |
| 2009/0171133 A1 | | 7/2009 | Luo et al. |
| 2011/0282114 A1 | | 11/2011 | Luo et al. |
| 2016/0167012 A1 | | 6/2016 | Xu et al. |
| 2017/0189884 A1 | | 7/2017 | Xu |
| 2017/0197195 A1 | | 7/2017 | Luo et al. |

OTHER PUBLICATIONS

PCT International Search Report, International Patent Appl. No. PCT/IB2018/056664, dated Mar. 7, 2019.

* cited by examiner

INTEGRATED REACTOR SYSTEM FOR IONIC LIQUID-CATALYZED HYDROCARBON CONVERSION

TECHNICAL FIELD

This application is directed to an integrated reactor system for performing an ionic liquid-catalyzed hydrocarbon conversion and a process using the integrated reactor system.

SUMMARY

This application provides an integrated reactor system for performing an ionic liquid-catalyzed hydrocarbon conversion, comprising:

a. a bundle of a heat exchanger tubing that extends predominantly through an internal length of a hydrocarbon conversion reactor;

b. baffles extending across at least a portion of the hydrocarbon conversion reactor;

c. multiple high speed jet flow nozzles configured to direct an ionic liquid catalyst and reactants into the hydrocarbon conversion reactor, external to the heat exchanger tubing; and d. a settling zone internal to the hydrocarbon conversion reactor.

The present invention may suitably comprise, consist of, or consist essentially of, the elements in the claims, as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

GLOSSARY

"Hydrocarbon conversion" refers to a change in a molecular structure or composition of a hydrocarbon.

"Alkylation" is the transfer of an alkyl group from one molecule to another. The process combines an unsaturated light hydrocarbon (olefin) with an isoparaffin to produce one or more alkylate products.

"Isoparaffin" refers to any branched-chain isomer of a straight-chain alkane.

"Gasoline" is a liquid hydrocarbon used as a fuel in internal combustion engines. Gasoline has a carbon number of predominately four to twelve. An alkylate gasoline is a gasoline product of an alkylation reaction.

"Naphtha" is a lighter hydrocarbon product having a naphtha boiling range from 90° F. to 300° F. (32° C. to 149° C.).

"Jet fuel" is a type of aviation fuel designed for use in aircraft powered by gas-turbine engines. Jet fuel is a hydrocarbon product having a jet fuel boiling range. The term "jet fuel boiling range" refers to hydrocarbons having a boiling range from 250° F. to 550° F. (121° C. to 288° C.). Alkylate jet fuel is a jet fuel product of an alkylation reaction.

"Diesel fuel" is any liquid fuel used in diesel engines, whose fuel ignition takes place, without any spark, as a result of compression of the inlet air mixture and then injection of fuel. The term "diesel fuel boiling range" refers to hydrocarbons having a boiling range from 250° F. to 700° F. (121° C. to 371° C.). Alkylate diesel fuel is a diesel fuel product of an alkylation reaction.

A "gasoline blending component" may be either a gasoline or a naphtha suitable for blending into a gasoline. Alkylate gasoline blending component is a gasoline blending component product of an alkylation reaction.

"Base oil" refers to a hydrocarbon fluid to which other oils or substances are added to produce a lubricant. An alkylate base oil is a base oil product of an alkylation reaction.

"Middle distillate", in the context of this disclosure, refers to liquid hydrocarbons having a boiling range from 240° F. to 725° F. (115.6° C. to 385° C.). In one embodiment, an alkylate middle distillate has a boiling range between the boiling ranges of an alkylate gasoline and an alkylate base oil.

"Predominantly", in the context of this disclosure, means 80 to 100%.

DETAILED DESCRIPTION

Ionic liquids can be used as catalysts for various types of hydrocarbon conversions. In one embodiment, the ionic liquid catalyst is an acidic ionic liquid. Examples of these hydrocarbon conversions include: alkylation, isomerization, hydrocracking, polymerization, dimerization, oligomerization, disproportionation, reverse disproportionation, acylation, metathesis, copolymerization, hydroformylation, dehalogenation, dehydration, and combinations thereof. In one embodiment the hydrocarbon conversion is alkylation of paraffins with olefins. Examples of ionic liquid catalysts and their use for alkylation of paraffins with olefins are taught, for example, in U.S. Pat. Nos. 7,432,408 and 7,432,409, 7,285,698, and U.S. patent application Ser. No. 12/184,069, filed Jul. 31, 2008. In one embodiment, the ionic liquid catalyst is a composite ionic liquid catalyst, wherein the cations come from a hydrohalide of an alkyl-containing amine or pyridine, and the anions are composite coordinate anions coming from two or more metal compounds. In another embodiment the conversion of a hydrocarbon is alkylation of paraffins, alkylation of aromatics, or combinations thereof. Many of these hydrocarbon conversions are exothermic and require cooling to provide temperature control for the hydrocarbon conversion.

The integrated reactor system of this disclosure provides intimate and rapid mixing between hydrocarbon reactants and ionic liquid catalysts while simultaneously removing reaction heat with a heat exchanger that is internal to the hydrocarbon conversion reactor. In one embodiment, the integrated reactor system also separates a majority of the ionic liquid catalysts from the hydrocarbon products in the settling zone within the hydrocarbon conversion reactor.

Heat Exchanger:

To provide the cooling, the integrated reactor system comprises a bundle of a heat exchanger tubing that extends predominantly through an internal length of the hydrocarbon conversion reactor. The heat exchanger tubing is configured to conduct a coolant inside the heat exchanger tubing and provide effective temperature control for the hydrocarbon conversion that occurs in the hydrocarbon conversion reactor. A coolant is a fluid which flows through the heat exchanger tubing to prevent the integrated reactor system from overheating, transferring the heat produced by the integrated reactor system to other devices that either use or dissipate it. In one embodiment, the coolant has high thermal capacity, low viscosity, is low-cost, non-toxic, chemically inert, and neither causes nor promotes corrosion of the cooling system. The coolant can either keep its phase and stay liquid or gaseous, or can undergo a phase transition, with the latent heat adding to the cooling efficiency. The latter type of coolant, when used to achieve below-ambient temperature, is more commonly known as a refrigerant. In one embodiment, the coolant comprises water. The coolant may also comprise additives, such as corrosion inhibitors, antifreeze, and combinations thereof. Antifreeze, a solution of a suitable organic chemical (most often ethylene glycol, diethylene glycol, or propylene glycol) in water, can be used when a water-based coolant has to withstand temperatures below 0° C., or when its boiling point has to be raised. In one embodiment, the coolant can comprise betaine. Betaine is made from pure plant juice, and can therefore be less difficult to dispose of ecologically.

The bundle of the heat exchanger tubing has multiple lines of the tubing extending through the hydrocarbon conversion reactor. There may be one or more bundles of the heat exchanger tubing. The lines of the tubing in the hydrocarbon conversion reactor can be sized and the number selected to provide sufficient temperature control in the hydrocarbon conversion reactor. In one embodiment, for example, the number of the lines of the tubing extending through the hydrocarbon conversion reactor can be from 10 to 10,000, such as from 100 to 5,000. An example of a suitable configuration might be about 500 to 1500 lines of tubing in a hydrocarbon conversion reactor with a width from about 5 to 30 feet (about 1.524 to 9.144 meters). An inside diameter of the lines of tubing in a hydrocarbon conversion reactor with this width, for example, could be from $\frac{1}{16}$ inch (0.1588 cm) to 1.5 inches (3.81 cm).

Figure 1:
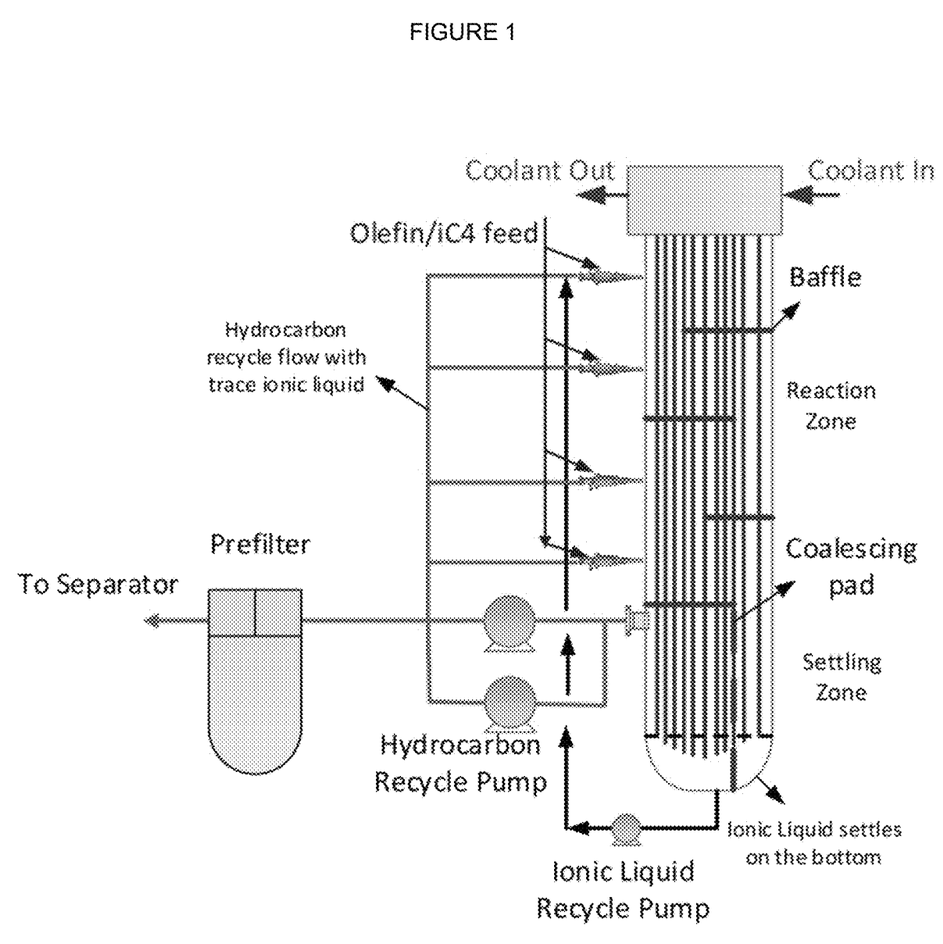
FIG. 1 is a schematic diagram of one embodiment of a vertically oriented integrated reactor system for ionic liquid-catalyzed hydrocarbon conversion.
Figure 2:
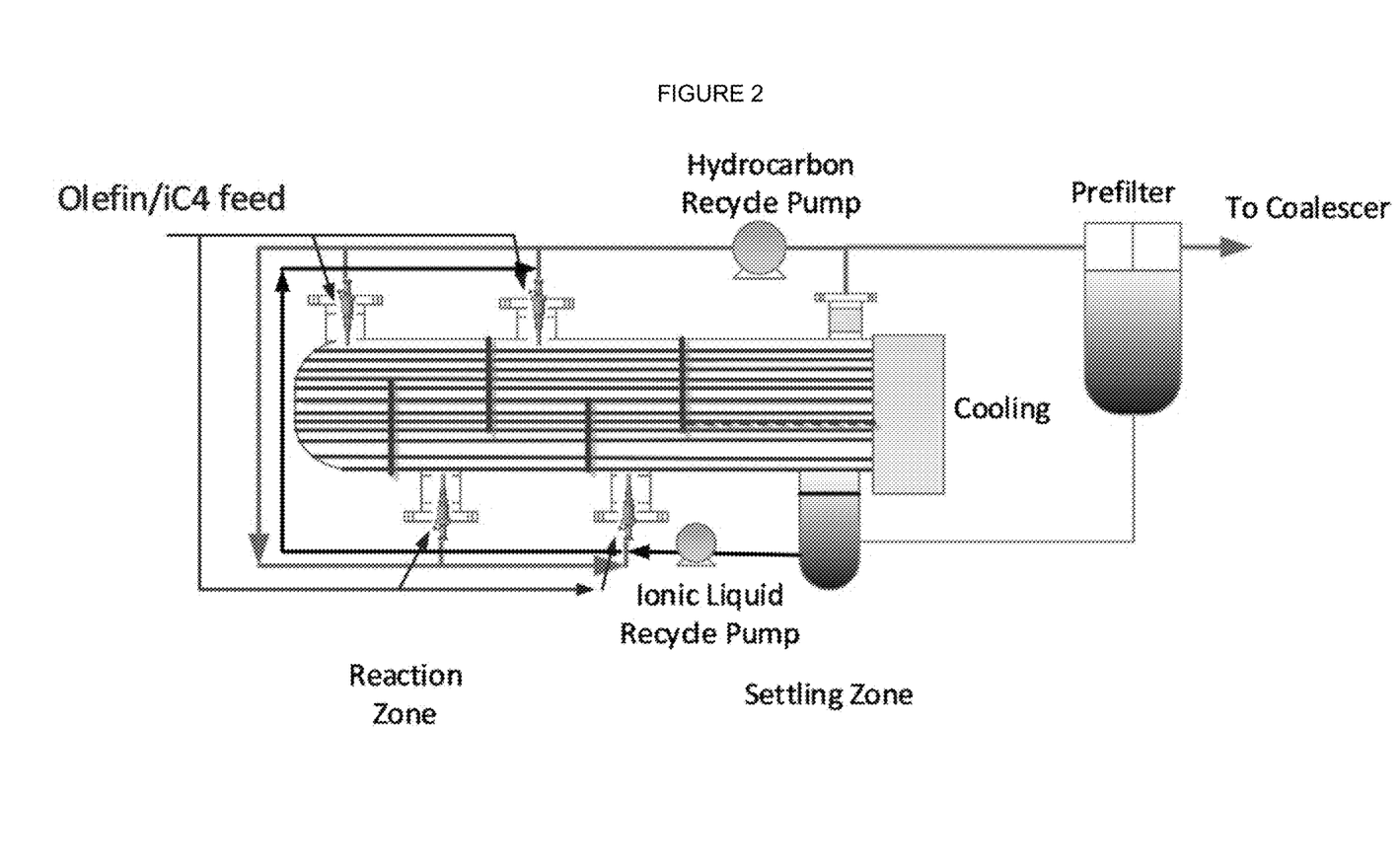
FIG. 2 is a schematic diagram of one embodiment of a horizontally oriented integrated reactor system for ionic liquid-catalyzed hydrocarbon conversion.
Figure 3:
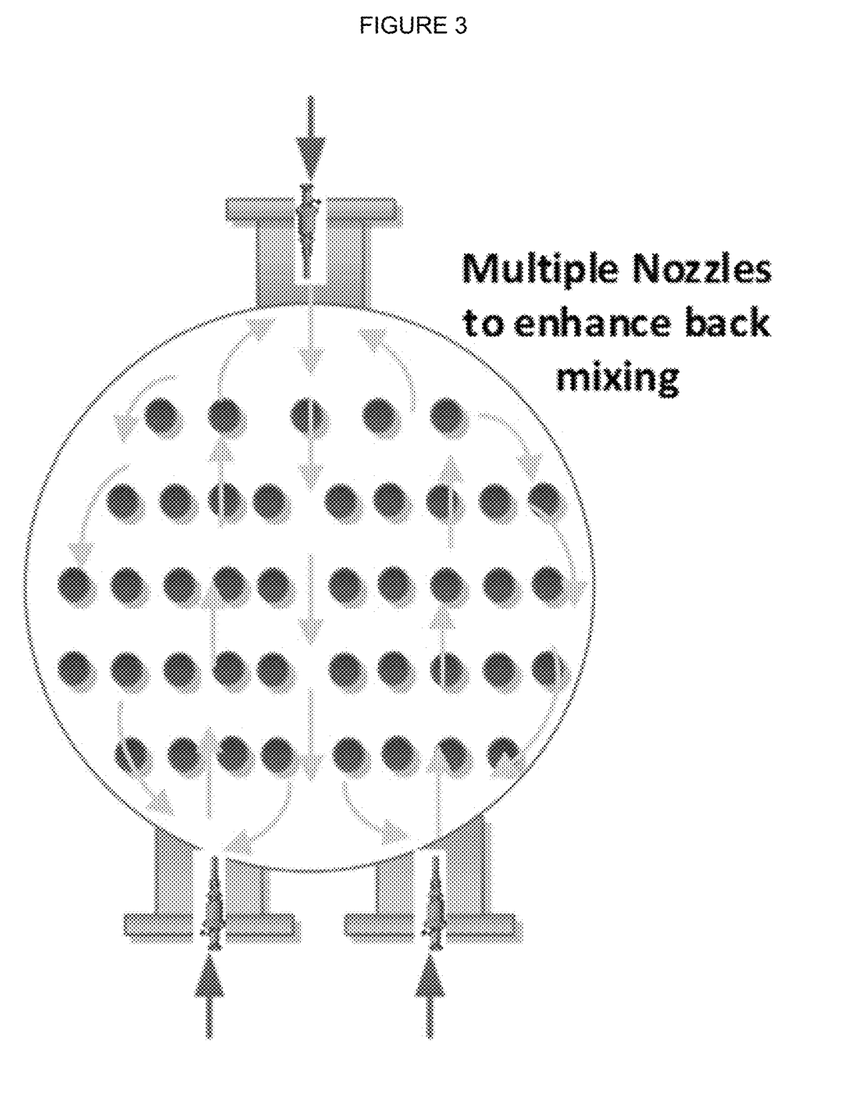
FIG. 3 is a schematic diagram of cross section of a hydrocarbon conversion reactor with an exemplary arrangement of three high speed jet flow nozzles.

In one embodiment, the bundle of the heat exchanger tubing extends through both a reaction zone and a settling zone in the hydrocarbon conversion reactor. This feature is shown in FIGS. 1 and 2.

In one embodiment, the lines of the tubing are arranged equidistant from each other and can be held in place. The spacing between the lines of tubing can be adjusted to provide the optimal cooling that is needed. In one embodiment, for example, the lines of tubing can be spaced from 1" to 5" from each other.

In one embodiment, the hydrocarbon conversion reactor has open channels into which the multiple high speed jet flow nozzles direct the reactants. In one embodiment, the heat exchanger tubing is arranged to have open channels inside the hydrocarbon conversion reactor into which the multiple high speed jet flow nozzles are configured to direct the reactants. The open channels can help direct a flow of the ionic liquid catalyst and the reactants and can also reduce a shear stress on the heat exchanger tubing. The channels can extend across a partial width or a full width of the hydrocarbon conversion reactor. The selection of the length of the open channels can be adjusted to provide the best combination of sufficient mixing of the ionic liquid catalyst and the reactants, effective cooling of a reaction mixture in the hydrocarbon conversion reactor, and low shear stress on the heat exchanger tubing.

In one embodiment, the bundle of the heat exchanger tubing is configured to minimize a flow resistance within the hydrocarbon conversion reactor, enhance a back-mixing of the reactants within the hydrocarbon conversion reactor, provide an effective heat transfer, and minimize a shear stress on the heat exchanger tubing caused by a flow of the reactants.

Baffles:

The integrated reactor system comprises baffles that extend across at least a portion of the hydrocarbon conversion reactor. In one embodiment, the lines of tubing can be held in place by the baffles. In one embodiment, the baffles provide support for the heat exchanger tubing. For example, the baffles could comprise a perforated plate through which the heat exchanger tubing extends.

In one embodiment, the baffles are placed in an alternating pattern and direct a flow of the reactants in a zig-zag direction through the hydrocarbon conversion reactor.

In one embodiment, the baffles are perpendicular to external walls of the hydrocarbon conversion reactor. In another embodiment, the baffles are angled to further direct the flow of the reactants and enhance back mixing within the hydrocarbon conversion reactor.

In one embodiment, the baffles separate the hydrocarbon conversion reactor into multiple sections. The multiple sections can occur in a series along the length of the hydrocarbon conversion reactor. In one embodiment, each section may comprise one or more of the high speed jet flow nozzles.

Hydrocarbon Conversion Reactor:

In one embodiment, the hydrocarbon conversion reactor is configured to provide a turbulent back flow of the reactants in the hydrocarbon conversion reactor. For example, the hydrocarbon conversion reactor can be configured to provide a turbulent back flow of the reactants in a reaction zone within the hydrocarbon conversion reactor. In one embodiment, the hydrocarbon conversion reactor is configured to prevent turbulence in the settling zone, which could adversely affect the efficiency of ionic liquid settling and separation. The turbulent back flow can be created and enhanced via one or more of the placement of the multiple high speed jet flow nozzles, the placement and width of the baffles, an orientation of the heat exchanger tubing, an internal diameter of the heat exchanger tubing, and a spacing of the heat exchanger tubing. In one embodiment, the turbulent back flow improves the yield and selectivity of the hydrocarbon conversion in the integrated reactor system.

The hydrocarbon conversion reactor, or the entire integrated reactor system, may be oriented in any direction, including vertically or horizontally. A vertically oriented hydrocarbon conversion reactor is shown in FIG. 1 and a horizontally oriented hydrocarbon conversion reactor is shown in FIG. 2.

In one embodiment, the hydrocarbon conversion reactor is designed to perform the ionic liquid-catalyzed hydrocarbon conversion in a liquid hydrocarbon phase. In one embodiment, the liquid hydrocarbon phase is a continuous phase and the ionic liquid catalyst is a dispersed phase in the hydrocarbon conversion reactor.

In one embodiment, the ionic liquid catalyst and other hydrocarbon liquids in the hydrocarbon conversion reactor move from one end of the hydrocarbon conversion reactor to the other end. In one embodiment, fine droplets of the ionic liquid catalyst will pass through a reaction zone in the hydrocarbon conversion reactor without significant, or any, pooling. In one embodiment, some large droplets of the ionic liquid catalyst will settle and accumulate inside of the reaction zone, but will not adversely affect the ionic liquid-catalyzed hydrocarbon conversion that occurs in the hydrocarbon conversion reactor. In one embodiment, less than 1/10 of the volume of the ionic liquid catalyst that is fed to the hydrocarbon conversion reactor settles out of a mixture in the reaction zone in the hydrocarbon conversion reactor. For example, a small amount of the ionic liquid catalyst may collect on the top of horizontally oriented baffles in the reactor, but a turbulent flow is retained.

In one embodiment, the hydrocarbon conversion reactor is designed to perform an alkylation. The alkylating conditions can be selected to provide the desired alkylate product yields and quality. The alkylation reaction is generally carried out in a liquid hydrocarbon phase in the hydrocarbon conversion reactor that is an alkylation reactor.

Catalyst volume in the hydrocarbon conversion reactor, such as in an alkylation reactor, can be in the range of 0.25 vol % to 50 vol %, for example from 1 vol % to 25 vol %, or from 3 vol % to 10 vol %. In some embodiments, only a very small amount of the ionic catalyst is needed, such as less than 10 vol % in the hydrocarbon conversion reactor, which results in a dispersed ionic liquid catalyst phase in a continuous hydrocarbon phase. The multiple high speed jet flow nozzles in the configurations disclosed herein provide an intimate mixing of the reactants with the ionic liquid catalyst and provide fine droplets of the ionic liquid catalyst with sufficient interfacial area for the hydrocarbon conversion.

In one embodiment, a hydrocarbon conversion temperature can be in the range from −40° C. to 150° C., such as −20° C. to 100° C., or −15° C. to 50° C. The pressure in the hydrocarbon conversion reactor can be in the range from atmospheric pressure to 8000 kPa. In one embodiment the pressure is kept sufficient to keep the reactants in a liquid phase. The residence time of reactants in the hydrocarbon conversion reactor can be in the range of a second to 10 hours. Examples of residence times that can be used include 0.5 min to 120 min, 1 min to 30 min, 1 min to 10 min, and 2 min to 5 min.

In one embodiment, one or more alkylate products are produced by the integrated reactor system, and the one or more alkylate products is one or more of an alkylate gasoline, an alkylate middle distillate, or an alkylate base oil. In one embodiment, the one or more alkylate products that are produced by the integrated reactor system are selected from the group consisting of an alkylate gasoline, an alkylate jet fuel, an alkylate diesel fuel, an alkylate base oil, and mixtures thereof.

High Speed Jet Flow Nozzles:

The high speed jet flow nozzles are configured to direct an ionic liquid catalyst and reactants into the hydrocarbon conversion reactor, external to the heat exchanger tubing. The high speed flow from the high speed jet flow nozzles can be greater than 0.8 m/s, such as from 1 m/s to 100 m/s, from 5 m/s to 50 m/s, or from 10 m/s to 30 m/s. In one embodiment, the high speed jet flow nozzles provide intimate and rapid mixing between the hydrocarbon reactant and the ionic liquid catalyst while simultaneously removing a reaction heat. A flow of the ionic liquid catalyst and the reactants occurs outside of the heat exchanger tubing.

In one embodiment, the high speed jet flow nozzles are placed along an external length of the hydrocarbon conversion reactor. They can be configured to not only direct the ionic liquid catalyst and the reactants, but also to provide sufficient mixing of the reactants with the ionic liquid catalyst. In one embodiment, the reactants are a continuous phase and the ionic liquid catalyst is a dispersed phase in the hydrocarbon conversion reactor.

In one embodiment, the high speed jet flow nozzles are arranged to enhance a back mixing inside the hydrocarbon conversion reactor. In one embodiment, the multiple high speed jet flow nozzles are placed along one side of the hydrocarbon conversion reactor. This embodiment, is shown in FIG. 1. In another embodiment, the multiple high speed jet flow nozzles are placed on opposing sides of the hydrocarbon conversion reactor, such as shown in FIGS. 2, 3, 5A, and 5B. Multiple high speed jet flow nozzles can be placed into each section of the hydrocarbon conversion reactor, one high speed jet flow nozzle can be placed into each section, or there may be a combination of these different configurations. In one embodiment, where there are multiple high speed jet flow nozzles in one section of the hydrocarbon conversion reactor, they may be arranged to direct their flows of the ionic liquid catalyst and the reactants to intersect at high speed. In one embodiment, the arrangement of the high speed jet flow nozzles is selected to: enhance a back-mixing inside the hydrocarbon conversion reactor, reduce a local olefin concentration, produce a better quality hydrocarbon product, or a combination thereof.

In one embodiment, the configuration of the multiple high speed jet flow nozzles is selected to increase a heat transfer coefficient that provides better reaction heat removal. In one embodiment, the configuration of the multiple high speed jet flow nozzles is selected to minimize a direct flow impact on the heat exchanger tubing. By minimizing the direct flow impact on the heat exchanger tubing, vibration and/or high stress on the heat exchanger tubing can be reduced or eliminated. In one embodiment, the avoidance of direct flow impact on the heat exchanger tubing can prevent, or significantly reduce, erosive wear of the heat exchanger tubing.

Figure 5A:
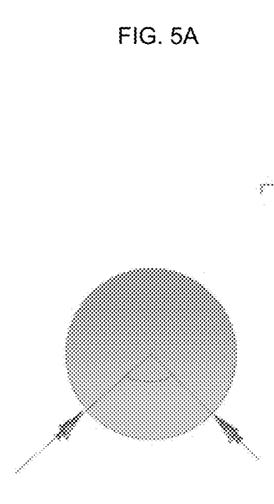
FIG. 5A is a schematic diagram of a cross section of a hydrocarbon conversion reactor with a pair of high speed jet flow nozzles that are arranged to intersect their directed flows.
Figure 5B:
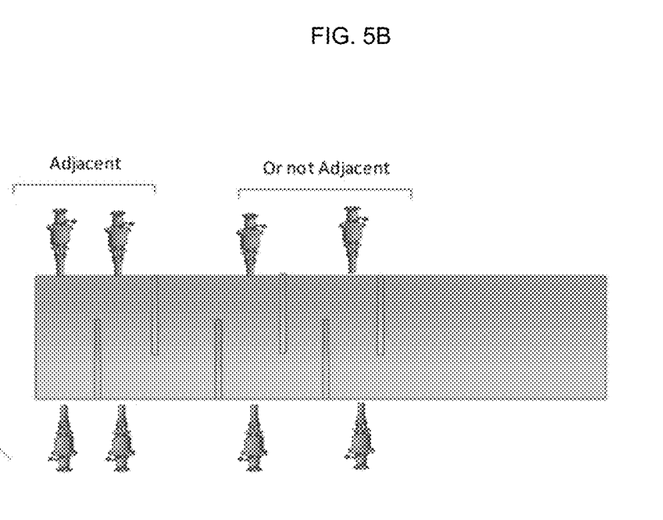
FIG. 5B is a schematic diagram showing both adjacent and non-adjacent arrangements of four pairs of high speed jet flow nozzles in a horizontally oriented hydrocarbon conversion reactor with six baffles (other features not shown).

In one embodiment, the multiple high speed jet flow nozzles are in one or more pairs. This embodiment can further enhance the mixing of the reactants with the ionic liquid catalyst. For example, the one or more pairs can be arranged so that directed flows of the ionic liquid catalyst and the reactants intersect at an angle from 1 to 180 degrees within the hydrocarbon conversion reactor. This feature is shown in FIGS. 5A and 5B. FIG. 5A shows one embodiment, wherein the ionic liquid catalyst and the reactants intersect at an angle of about 90 degrees. As shown in FIG. 5B, the pairs of the high speed jet flow nozzles can be placed with one pair per section of the hydrocarbon conversion reactor, either in adjacent sections defined by a baffle, in non-adjacent sections defined by baffles, or in a combination thereof.

In one embodiment, there can be many pairs of high speed jet flow nozzles with each pair directing the ionic liquid catalyst and the reactants so that they intersect each other at an intersection angle from 1 to 180 degrees. The intersection angles may vary across a length of the hydrocarbon conversion reactor.

In one embodiment, the multiple high speed jet flow nozzles are arranged to promote an alkylation. In one embodiment, the multiple high speed jet flow nozzles are designed to intimately mix an olefin feed, an isoparaffin feed, a recycled hydrocarbon stream, and a recycled ionic liquid stream. In one embodiment, the multiple high speed jet flow nozzles are arranged to divide an olefin feed into multiple streams that provide a high local molar ratio of an isoparaffin to an olefin at an injection point of each of the multiple high speed jet flow nozzles. This can be a useful embodiment to perform an alkylation, such as to make an alkylate gasoline blending component, an alkylate jet fuel, and alkylate diesel fuel, and combinations thereof. In one embodiment, an olefin feed is divided into multiple streams that are fed by the high speed jet flow nozzles at different locations along the hydrocarbon conversion reactor, which can result in a low olefin local concentration at injection points. A high local molar ratio of the isoparaffin to the olefin at the injection points of the high speed jet flow nozzles can increase an octane number and lower a final boiling point of the alkylate gasoline that is produced.

In one embodiment, the olefin feeds that can be used include $C_2$-$C_{43}$ olefins from any source and in any combination. In one embodiment, the isoparaffin feeds that can be used include $C_3$-$C_{50}$ isoparaffins from any source and in any combination. The selection of the olefin feed and the isoparaffin feed can be selected based on the hydrocarbon products that are to be produced in the integrated reactor system.

Settling Zone:

The integrated reactor system comprises a settling zone internal to the hydrocarbon conversion reactor. The settling zone can provide a separation of the ionic liquid catalyst from the reactants or the hydrocarbon products produced in the hydrocarbon conversion reactor. In one embodiment, the settling zone comprises a gravity separator. In one embodiment, the settling zone is at a bottom or one end of the hydrocarbon conversion reactor. In one embodiment, the settling zone is below a reaction zone in the hydrocarbon conversion reactor. In one embodiment, the settling zone is from 5% to 75% the internal length of the hydrocarbon conversion reactor.

In one embodiment a density of the ionic liquid catalyst is sufficiently greater than the density of the reactants or the hydrocarbon products produced in the hydrocarbon conversion reactor such that the ionic liquid catalyst separates effectively in the settling zone. In one embodiment, a difference between the density of the ionic liquid catalyst and the density of the reactants or the hydrocarbon products is at least 0.1 g/mL, such as from 0.1 to 3.0 g/mL. Density can be measured by ASTM D4052-16, *Standard Test Method for Density, Relative Density, and API Gravity of Liquids by Digital Density Meter.*

In one embodiment, the settling zone comprises at least one coalescing pad. This feature is shown in FIGS. 1 and 2. In one embodiment, the at least one coalescing pad can comprise multiple layers of media with a large pore size that remove a substantial amount of ionic liquid droplets from the hydrocarbon reactants and hydrocarbon products, e.g., over 50% of ionic liquid droplets can be removed, such as from 60% to 95%. A large pore size can be from greater than 100 microns to 100,000 microns. In one embodiment, the at least one coalescing pad can comprise multiple layers of media having a fine pore size of 100 microns or less, or even 20 microns or less. In one embodiment, at least one coalescing pad comprises multiple layers of media having the fine pore size of 1 to 100 microns. In one embodiment, the settling zone equipped with at least one coalescing pad is able to remove over 90%, more preferably over 95%, of ionic liquid droplets from hydrocarbon reactants and hydrocarbon products. In one embodiment, the at least one coalescing pad can comprise multiple layers of media with different pore sizes. In one embodiment, the settling zone removes from 90 to 100% of the ionic liquid droplets from the hydrocarbon reactants and hydrocarbon products.

The coalescing pad provides separation of the ionic liquid catalyst from any remaining hydrocarbon reactants and hydrocarbon products produced in the hydrocarbon conversion reactor. The ionic liquid catalyst settles at the bottom of the hydrocarbon conversion reactor. In one embodiment, the multiple layers of media can be arranged to have alternating hydrophilic surface properties and hydrophobic surface properties. Examples of media having hydrophilic surface properties include various metals, including metal alloys. In one embodiment, the metal media provides structural support for the other media in the coalescing pad. In a sub-embodiment, one or more layers of media with the hydrophilic surface properties in the at least one coalescing pad comprise a metal. Examples of hydrophobic media having hydrophobic surface properties include materials made from hydrocarbons, including engineered polymers. Examples of engineered polymers include fiberglass, epoxy resins, polyester resins, vinylesters, thermoplastic resins, acrylic/phenolic resin, nylon, or combinations thereof. In one embodiment, the media having hydrophobic surface properties comprise a fiberglass. In one embodiment, the media having hydrophobic surface properties comprises a polyester material. Other examples of engineered polymers include polybutylene terephthalate (PBT), polyamide materials, fluoropolymer, polyolefin or a media obtained by treating a fibrous engineered polymer with an agent comprising fluorine functionalities.

In one embodiment, the separated hydrocarbon stream collects in a top portion of the settling zone. In one embodiment, the integrated reactor system comprises an exit port in the top portion of the settling zone that elutes a separated hydrocarbon stream that is recycled in part to the hydrocarbon conversion reactor. This feature is shown in FIGS. 1 and 2. In one embodiment, the exit port in the top portion of the settling zone elutes the hydrocarbon products produced in the hydrocarbon conversion reactor. These hydrocarbon products can then be sent as a slipstream for further processing and cleanup, such as to a prefilter and a separator or to a prefilter and a coalescer. The hydrocarbon products could then be sent to a distillation column for further product separation.

In one embodiment, the integrated reactor system additionally comprises one or more prefilters, connected to one or more coalescers, that receive an effluent from the hydrocarbon conversion reactor and remove entrained ionic liquid from the hydrocarbon products in the effluent.

In one embodiment, a separated ionic liquid collects in the bottom of the settling zone. In one embodiment, the integrated reactor system comprises a lower exit port in a bottom portion of the settling zone that elutes a separated ionic liquid. The separated ionic liquid can be recycled to the hydrocarbon conversion reactor.

In one embodiment, a bottom of the settling zone is sufficiently large to collect and store an ionic liquid, and to function as a surge volume for the ionic liquid catalyst. In one embodiment, a slip stream of the ionic liquid from a bottom of the settling zone can be sent via a connection between the bottom of the settling zone to an ionic liquid regeneration unit or a purge unit, allowing the ionic liquid catalyst to maintain high catalytic strength. In one embodiment, a make-up fresh ionic liquid can be introduced via an ionic liquid inlet at the bottom of the settling zone to allow a sufficient ionic liquid volume within the hydrocarbon conversion reactor to perform the ionic liquid-catalyzed hydrocarbon conversion.

In one embodiment, the settling zone may additionally comprise a boot. This feature is shown at the bottom of the settling zone in FIG. 2. The boot can be connected to the lower exit port and placed before an ionic liquid recycle pump. The boot may also be connected to a prefilter, which feeds residual ionic liquid catalyst removed by the prefilter to the boot. In one embodiment, the boot is additionally connected to the bottom of the prefilter, wherein the prefilter is connected to an exit port in a top portion of the settling zone. The integration of the boot with the prefilter can improve the separation efficiency of a downstream coalescer.

Reactant and Catalyst Recycling:

In one embodiment, the integrated reactor system comprises at least one ionic liquid recycle pump and at least one hydrocarbon recycle pump that are fluidly connected to the multiple high speed jet flow nozzles. In one embodiment, the integrated reactor system comprises an exit port in the top portion of the settling zone that elutes a separated hydrocarbon stream that is recycled to the hydrocarbon conversion reactor. The separated hydrocarbon stream can contain only trace amounts of fine droplets of the ionic liquid catalyst.

Figure 4:
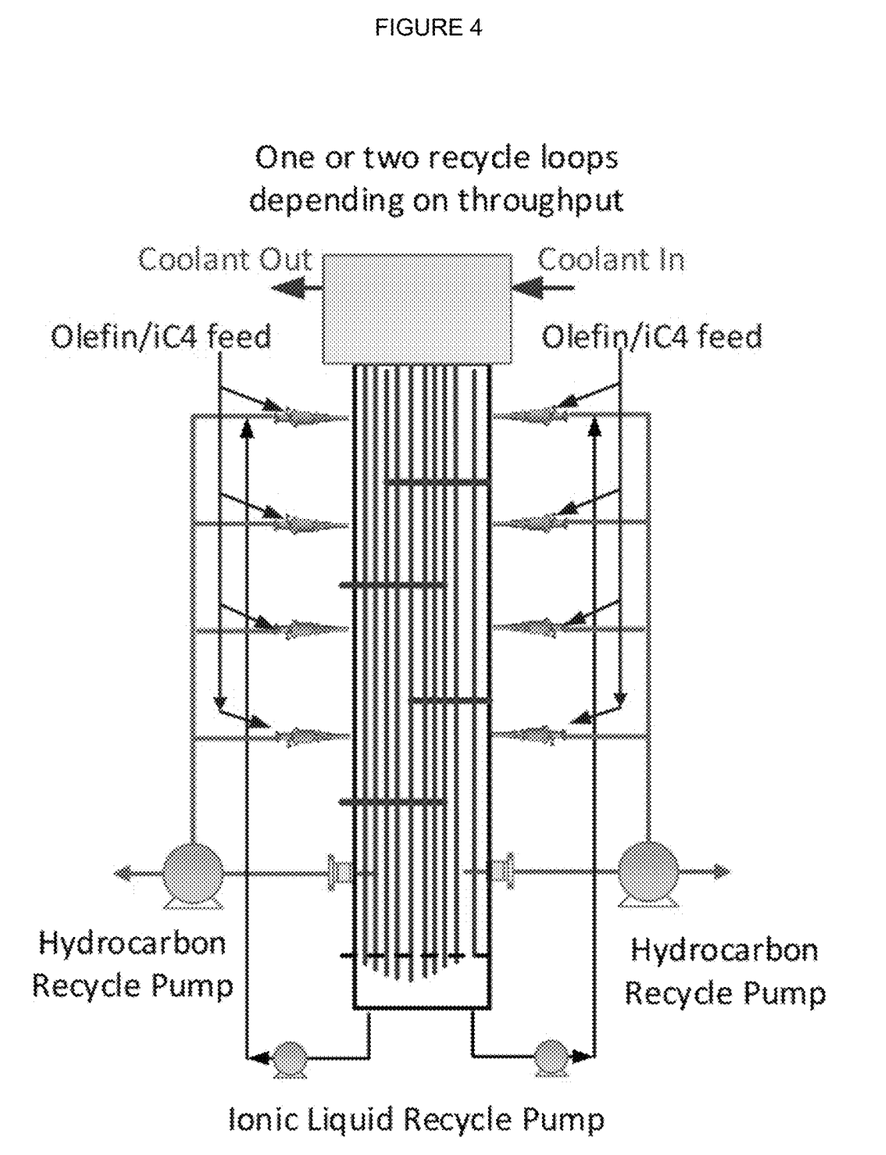
FIG. 4 is a schematic diagram of one embodiment of an integrated reactor system having multiple recycle loops.

In one embodiment, the integrated reactor system comprises one or more recycle loops for both a recycled hydrocarbon stream and a recycled ionic liquid stream. FIG. 4 shows an embodiment with two recycle loops, with each loop being configured for operating independently. Multiple recycle loops can be beneficial for large-scale integrated reactor systems where the smaller recycle loops can be sized to improve the cost and the operation of the integrated reactor system. In one embodiment, each recycle loop can be operated independently, reducing the need for expensive backup pumps and their associated control systems. In one embodiment, there can be two or more recycle loops and each of the two or more recycle loops is configured to operate independently.

In one embodiment, one or more ionic liquid recycle pumps are connected to the bottom of the settling zone and recycle the ionic liquid catalyst to the high speed jet flow nozzles.

In one embodiment, the integrated reactor system produces an alkylate gasoline or an alkylate gasoline blending component with a high octane number. Examples of high octane numbers are 82 or higher, greater than 85, greater than 90, and greater than 95. In one embodiment the alkylate gasoline or the alkylate gasoline blending component has a Research-method octane number (RON) from 90 to 105. Different methods are used for calculating octane numbers of fuels or fuel blend components. RON can be determined using ASTM D2699-16$\varepsilon^1$. RON employs the standard Cooperative Fuel Research (CFR) knock-test engine. Additionally, the Research-method octane number may be calculated [RON (GC)] from gas chromatography boiling range distribution data. The RON (GC) calculation is described in the publication, Anderson, P. C., Sharkey, J. M., and Walsh, R. P., "Journal Institute of Petroleum", 58 (560), 83 (1972).

Alkylation processes for making alkylate gasoline with low volatility and high octane number are described in U.S. Pat. Nos. 7,432,408 and 7,919,663.

In one embodiment, wherein the one or more olefins comprise a 2-butene and the isoparaffin is an isobutane, the one or more alkylate products produced in the hydrocarbon conversion reactor is an alkylate gasoline or an alkylate gasoline blending component with a high RON, such as having a RON of 85 or higher, or from 90 to 105.

FIGS. 1 & 2, for example, show two different embodiments for an integrated reactor system that can perform an alkylation to make a high quality alkylate gasoline blending component.

This application provides processes to make an alkylate gasoline blending component, an alkylate jet fuel, an alkylate diesel fuel, an alkylate base oil, or combinations thereof, comprising: performing an alkylation of an isoparaffin with an olefin in the integrated reactor systems disclosed herein.

Exemplary alkylation processes for making an alkylate base oil with high viscosity index and low bromine index are described in "HIGH VISCOSITY INDEX LUBRICANTS BY ISOALKANE ALKYLATION", U.S. patent application Ser. No. 15/159,205, filed on May 19, 2016.

Exemplary alkylation processes for making alkylate gasoline and alkylate middle distillate are described in U.S. Pat. No. 8,252,968.

Ionic Liquid Catalyst:

The ionic liquid catalyst is composed of at least two components which form a complex. In one embodiment, the ionic liquid catalyst is acidic. The acidic ionic liquid catalyst comprises a first component and a second component. The first component of the catalyst will typically comprise a Lewis Acidic compound selected from components such as Lewis Acidic compounds of Group 13 metals, including aluminum halides, alkyl aluminum halides, gallium halides, alkyl gallium halides, indium halids, and alkyl indium halides (see International Union of Pure and Applied Chemistry (IUPAC), version 3, October 2005, for Group 13 metals of the periodic table). Other Lewis Acidic compounds besides those of Group 13 metals may also be used. In one embodiment the first component is aluminum halide or gallium halide or iron halide or alkyl aluminum halide. In one embodiment, the first component is aluminum halide or alkyl aluminum halide. For example, aluminum trichloride may be used as the first component for preparing the ionic liquid catalyst.

The second component making up the ionic liquid catalyst is an organic salt or mixture of salts. These salts may be characterized by the general formula $Q^+A^-$, wherein $Q^+$ is an ammonium, phosphonium, boronium, iodonium, or sulfonium cation and $A^-$ is a negatively charged ion, such as $Cl^-$, $Br^-$, $ClO_4^-$, $NO_3^-$, $BF_4^-$, $BC_4^-$, $PF_6^-$, $SbF_6^-$, $AlCl_4^-$, $ArF_6^-$, $TaF_6^-$, $CuCl_2^-$, $FeCl_3^-$, $HSO_3^-$, $RSO_3^-$ (wherein R is an alkyl group having from 1 to 12 carbon atoms), $SO_3CF_3^-$, $SO_3Cl^-$, and 3-sulfurtrioxyphenyl. In one embodiment the second component is selected from those having quaternary ammonium or phosphonium halides containing one or more alkyl moieties having from about 1 to 12 carbon atoms, such as, for example, trimethylamine hydrochloride, methyltributylammonium halide, trialkyl phosphonium hydrochloride, tetraalkylphosphonium chlorides, methyltrialkylphosphonium halide, or substituted heterocyclic ammonium halide compounds, such as 1-butylpyridinium halide, or hydrocarbyl substituted imidazolium halides, such as for example, 1-ethyl-3-methyl-imidazolium chloride. In one embodiment, the ionic liquid catalyst is a highly acidic chloroaluminate ionic liquid. In one embodiment the ionic liquid catalyst is a chloroaluminate ionic liquid having the general formula R R' R" N H$^+$ Al$_2$Cl$_7^-$ or R R' R" P H$^+$ Al$_2$Cl$_7^-$, wherein R, R', and R" are alkyl groups containing 1 to 12 carbons. Examples of highly acidic chloroaluminate ionic liquids are those comprising $Al_2Cl_7^-$ and $Al_3Cl_{10}^-$.

In one embodiment, the ionic liquid catalyst comprises an alkyl substituted pyridinium chloroaluminate or an alkyl substituted imidazolium chloroaluminate of the general formulas A and B, respectively.

In the formulas A and B, R is H, methyl, ethyl, propyl, butyl, pentyl or hexyl group, R'=H, methyl, ethyl, propyl, butyl, pentyl or hexyl group, X is a chloroaluminate, and $R_1$ and $R_2$ are H, methyl, ethyl, propyl, butyl, pentyl or hexyl group. The ionic liquid catalyst may also comprise a derivative of either of the structures A or B in which one or more of the hydrogens attached directly to carbon in the ring has been replaced by an alkyl group. In the formulas A and B: R, R', $R_1$ and $R_2$ may or may not be the same. Alternatively the ionic liquid catalyst is a chloroaluminate ionic liquid having the general formula R R' R" R''' $N^+ Al_2Cl_7^-$ or R R' R" R''' $P Al_2Cl_7^-$, wherein R, R', R" and R''' are alkyl groups containing 1 to 12 carbons.

The presence of the first component should give the ionic liquid a Lewis or Franklin acidic character. Generally, the greater the mole ratio of the first component to the second component, the greater the acidity of the ionic liquid mixture. In one embodiment, a molar ratio of the first component (metal halide) to the second component (quaternary amine or quaternary phosphorus) in the ionic liquid catalyst is in the range of 2:1 to 1.1:1.

Ionic Liquid Co-Catalyst:

In one embodiment, a co-catalyst is added to the ionic liquid catalyst to boost the overall acidity and change the selectivity of the ionic liquid catalyst. The co-catalyst can be a halide containing additive, such as a co-catalyst comprising a chloride. The halide containing additive can be selected, and added to the ionic liquid catalyst, to provide increased yield of an alkylate product. Examples of halide containing additives are hydrogen halide, alkyl halide, metal halide, and combinations thereof. In one embodiment, the halide containing additive may be a Bronsted acid. Examples of Bronsted acids are hydrochloric acid (HCl), hydrobromic acid (HBr), and trifluoromethanesulfonic acid. The use of halide containing additives with ionic liquid catalysts is disclosed in U.S. Published Patent Application Nos. 2003/0060359 and 2004/0077914. In one embodiment the halide containing additive is a fluorinated alkane sulphonic acid having the general formula:

wherein R'=Cl, Br, I, H, an alkyl or perfluoro alkyl group, and R"=H, alkyl, aryl or a perfluoro alkoxy group.

Examples of metal halides that may be used are NaCl, LiCl, KCl, $BeCl_2$, $CaCl_2$, $BaCl_2$, $SrCl_2$, $MgCl_2$, $PbCl_2$, CuCl, $CuCl_2$, $ZrCl_4$ and AgCl, as described by Roebuck and Evering (Ind. Eng. Chem. Prod. Res. Develop., Vol. 9, 77, 1970). In one embodiment, the halide containing additive contains one or more IVB metal compounds, such as $ZrCl_4$, $ZrBr_4$, $TiCl_4$, $TiCl_3$, $TiBr_4$, $TiBr_3$, $HfCl_4$, or $HfBr_4$, as described by Hirschauer et al. in U.S. Pat. No. 6,028,024.

In one embodiment, the halide containing additive is added at a level that provides increased yield of an alkylate jet fuel or an alkylate diesel fuel. Adjusting the level of the halide containing additive level can change the selectivity of an alkylation reaction. For example, when the level of the halide containing additive, e.g., hydrochloric acid, is adjusted lower, the selectivity of the alkylation reaction shifts towards producing heavier products. The effects of increasing a molar ratio of olefin to HCl in the feed to an ionic liquid alkylation reactor (adjusting the level of the hydrochloric acid lower) on the yield of C10+ products in the alkylate produced is described in U.S. Pat. No. 7,919,664.

In one embodiment, a co-catalyst comprising a chloride is added to the ionic liquid catalyst. In one embodiment, the co-catalyst comprising a chloride that is added to the ionic liquid catalyst is an alkyl halide that generates anhydrous HCl in the alkylation reactor.

The transitional term "comprising", which is synonymous with "including," "containing," or "characterized by," is inclusive or open-ended and does not exclude additional, un-recited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

The invention illustratively disclosed herein suitably may be practiced in the absence of any element which is not specifically disclosed herein.

It should be noted that only the components relevant to the disclosure are shown in the figures, and that many other components normally part of an integrated reactor system for making one or more hydrocarbon products are not shown for simplicity.

EXAMPLES

Example 1

A Computational Fluid Dynamic (CFD) simulation was conducted for one embodiment of the integrated reactor system of this disclosure. In this embodiment, a vertical hydrocarbon conversion reactor was separated into multiple connecting segments, with six horizontal baffles. The reaction zone in the hydrocarbon conversion reactor had six segments on the top of the reactor and the settling zone was one segment at the bottom of the reactor. Three high speed jet flow nozzles were used to intimately mix an olefin feed and an isoparaffin feed with the hydrocarbon recycle stream and the ionic liquid recycle stream and to introduce the combined flow into the reaction zone at high speed. The high speed jet flow nozzles were oriented horizontally along the side of the vertical hydrocarbon conversion reactor, as shown in FIGS. 6A and 6B.

To simplify the simulation, the olefin/isoparaffin feed was assumed to have completely mixed with the hydrocarbon/ionic liquid recycle streams at the inlets of the high speed jet flow nozzles, resulting in well mixed streams containing a continuous hydrocarbon phase and a dispersed ionic liquid phase. To further simplify the simulation, it was further assumed that the dispersed ionic liquid phase comprised ionic liquid droplets having a same fixed diameter. Droplet coalescing and breakup were not considered in the simulation.

Figure 6A:
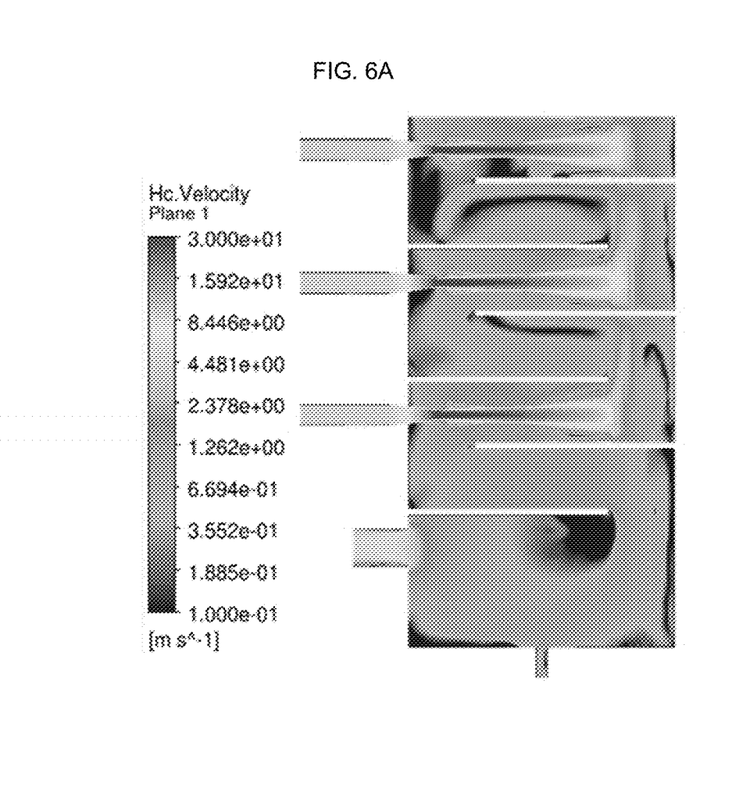
FIG. 6A shows the liquid velocity profile for one embodiment of the integrated reactor system, predicted by Computational Fluid Dynamics (CFD) simulations.
Figure 6B:
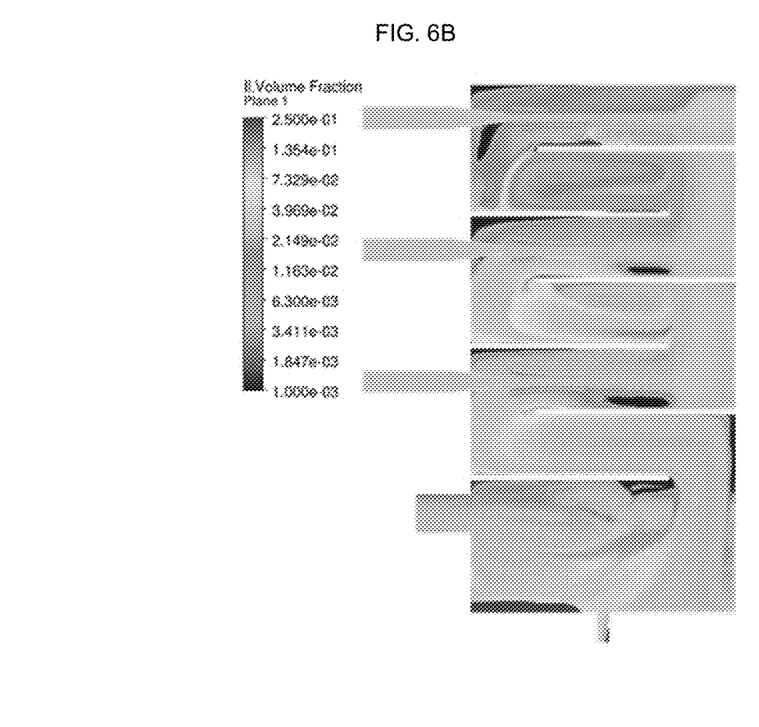
FIG. 6B shows the catalyst volume fraction profile for one embodiment of the integrated reactor system, predicted by CFD simulations

FIG. 6A shows the CFD simulated liquid velocity profile in the hydrocarbon conversion reactor, and FIG. 6B shows the CFD simulated ionic liquid concentration profile in the same hydrocarbon conversion reactor. In these figures, the colors represent the magnitude of the variables based on the color maps shown to the left of each figure. A red color indicates a high value, while a blue color indicates a low value.

As shown in FIG. 6A, the high speed jet flow nozzles produced high speed flow that resulted in high liquid back mixing, and therefore liquid turbulence, within the reaction zone. The high liquid back mixing and liquid turbulence would be highly effective to carry out a fast and selective hydrocarbon conversion reaction. Further shown in FIG. 6B, the high liquid flow and liquid turbulence resulted in a rather uniform ionic liquid concentration in the entire reaction zone, except on small portions at the top of the baffles where some of the ionic liquid droplets settled and accumulated.

It is claimed:

1. An integrated reactor system for performing an ionic liquid-catalyzed hydrocarbon conversion, comprising:
   a. a bundle of a heat exchanger tubing that extends predominantly through an internal length of a hydrocarbon conversion reactor;
   b. baffles extending across at least a portion of the hydrocarbon conversion reactor;
   c. multiple high speed jet flow nozzles configured to direct an ionic liquid catalyst and reactants into the hydrocarbon conversion reactor, external to the heat exchanger tubing; and
   d. a settling zone internal to the hydrocarbon conversion reactor, wherein the settling zone comprises at least one coalescing pad.

2. The integrated reactor system of claim 1, wherein the hydrocarbon conversion reactor is oriented vertically or horizontally.

3. The integrated reactor system of claim 1, wherein the baffles are placed in an alternating pattern and direct a flow of the reactants in a zig-zag direction through the hydrocarbon conversion reactor.

4. The integrated reactor system of claim 1, wherein the baffles separate the hydrocarbon conversion reactor into multiple sections.

5. The integrated reactor system of claim 1, wherein the baffles provide support for the heat exchanger tubing.

6. The integrated reactor system of claim 1, wherein the heat exchanger tubing is arranged to have open channels inside the hydrocarbon conversion reactor into which the multiple high speed jet flow nozzles are configured to direct the reactants.

7. The integrated reactor system of claim 1, wherein the hydrocarbon conversion reactor has open channels into which the multiple high speed jet flow nozzles direct the reactants.

8. The integrated reactor system of claim 1, wherein the multiple high speed jet flow nozzles are placed along an external length of the hydrocarbon conversion reactor.

9. The integrated reactor system of claim 1, wherein the multiple high speed jet flow nozzles are arranged to enhance a back mixing inside the hydrocarbon conversion reactor.

10. The integrated reactor system of claim 1, wherein the multiple high speed jet flow nozzles are designed to intimately mix an olefin feed, an isoparaffin feed, a recycled hydrocarbon stream, and a recycled ionic liquid stream.

11. The integrated reactor system of claim 1, wherein the multiple high speed jet flow nozzles are placed along one side of the hydrocarbon conversion reactor.

12. The integrated reactor system of claim 1, wherein the multiple high speed jet flow nozzles are in one or more pairs.

13. The integrated reactor system of claim 12, wherein the one or more pairs are arranged so that directed flows of the ionic liquid catalyst and the reactants intersect at an angle from 90 to 180 degrees within the hydrocarbon conversion reactor.

14. The integrated reactor system of claim 1, wherein the multiple high speed jet flow nozzles are arranged to divide an olefin feed into multiple streams that provide a high local molar ratio of an isoparaffin to an olefin at an injection point of each of the multiple high speed jet flow nozzles.

15. The integrated reactor system of claim 1, wherein a bottom of the settling zone is sufficiently large to collect and store the ionic liquid catalyst, and to function as a surge volume for the ionic liquid catalyst.

16. The integrated reactor system of claim 1, additionally comprising an exit port in a top portion of the settling zone that elutes a separated hydrocarbon stream that is recycled to the hydrocarbon conversion reactor.

17. The integrated reactor system of claim 1, additionally comprising an ionic liquid recycle pump and a hydrocarbon recycle pump that are fluidly connected to the multiple high speed jet flow nozzles.

18. The integrated reactor system of claim 1, comprising one or more recycle loops for both a recycled hydrocarbon stream and a recycled ionic liquid stream.

19. The integrated reactor system of claim 18, wherein there are two or more recycle loops and each of the two or more recycle loops is configured to operate independently.

20. A process to make an alkylate gasoline blending component, an alkylate jet fuel, an alkylate diesel fuel, an alkylate base oil, or combinations thereof, comprising: performing an alkylation of an isoparaffin with an olefin in the integrated reactor system of claim 1.

21. An integrated reactor system for performing an ionic liquid-catalyzed hydrocarbon conversion, comprising:
   a. a bundle of a heat exchanger tubing that extends predominantly through an internal length of a hydrocarbon conversion reactor;
   b. baffles extending across at least a portion of the hydrocarbon conversion reactor;
   c. multiple high speed jet flow nozzles configured to direct an ionic liquid catalyst and reactants into the hydrocarbon conversion reactor, external to the heat exchanger tubing; and
   d. a settling zone internal to the hydrocarbon conversion reactor;
additionally comprising a lower exit port in a bottom portion of the settling zone that elutes a separated ionic liquid that is recycled to the hydrocarbon conversion reactor; additionally comprising a boot, connected to the lower exit port and placed before an ionic liquid recycle pump, wherein the boot is additionally connected to the bottom of a prefilter, wherein the prefilter is connected to an exit port in a top portion of the settling zone.

22. An integrated reactor system for performing an ionic liquid-catalyzed hydrocarbon conversion, comprising:
   a. a bundle of a heat exchanger tubing that extends predominantly through an internal length of a hydrocarbon conversion reactor;
   b. baffles extending across at least a portion of the hydrocarbon conversion reactor;
   c. multiple high speed jet flow nozzles configured to direct an ionic liquid catalyst and reactants into the hydrocarbon conversion reactor, external to the heat exchanger tubing; and
   d. a settling zone internal to the hydrocarbon conversion reactor; additionally comprising one or more prefilters, connected to one or more coalescers, that receive an effluent from the hydrocarbon conversion reactor and remove entrained ionic liquid from hydrocarbon products in the effluent.

* * * * *